(12) United States Patent
Skrabelj et al.

(10) Patent No.: US 10,454,236 B2
(45) Date of Patent: Oct. 22, 2019

(54) LASER SYSTEM

(71) Applicant: Fotona d.o.o., Ljubljana (SI)

(72) Inventors: Dejan Skrabelj, Lesce (SI); Kranjec Jozica, Lesce (SI); Matjaz Lukac, Ljubljana (SI)

(73) Assignee: Fotona d.o.o., Ljubljana (SI)

(*) Notice: Subject to any disclaimer, the term of this patent is extended or adjusted under 35 U.S.C. 154(b) by 0 days.

(21) Appl. No.: 16/026,921

(22) Filed: Jul. 3, 2018

(65) Prior Publication Data
US 2019/0006815 A1 Jan. 3, 2019

(30) Foreign Application Priority Data

Jul. 3, 2017 (EP) .................................... 17001127

(51) Int. Cl.
*H01S 3/23* (2006.01)
*H01S 3/16* (2006.01)
(Continued)

(52) U.S. Cl.
CPC ........ *H01S 3/10061* (2013.01); *A61N 5/0616* (2013.01); *H01S 3/08054* (2013.01);
(Continued)

(58) Field of Classification Search
CPC .. H01S 2301/206; H01S 3/115; H01S 3/1103; H01S 3/23; H01S 3/081;
(Continued)

(56) References Cited

U.S. PATENT DOCUMENTS

| 4,918,704 A | * | 4/1990 | Caprara | .............. H01S 3/08081 |
| | | | | 372/10 |
| 2002/0051470 A1 | * | 5/2002 | Halmos | ................... H01S 3/113 |
| | | | | 372/10 |

(Continued)

FOREIGN PATENT DOCUMENTS

| WO | 2016/135638 A1 | 9/2016 | |
| WO | WO 2016/135638 | * 9/2016 | .............. H01S 3/115 |

OTHER PUBLICATIONS

European Search Report dated Jan. 12, 2018 of European application 17 001 127.4 on which this application is based.

*Primary Examiner* — Tuan N Nguyen
(74) *Attorney, Agent, or Firm* — Walter Ottesen, P.A.

(57) ABSTRACT

A laser system includes a first laser source with a laser resonator for generating a first pulsed laser beam. The resonator has a back mirror, an outcoupling mirror and an active lasing medium in between. The system includes a second laser source for generating a second pulsed laser beam and an optical block. The optical block includes a coupling polarizer and a first polarization rotator. The optical block is movable back and forth between an active position and a passive position. In its active position the optical block is located between the outcoupling mirror and the active lasing medium such that the coupling polarizer couples the second beam into the laser resonator of the first laser source while the first rotator is positioned between the outcoupling mirror and the coupling polarizer. In the active position of the optical block a second polarization rotator is between it and the back mirror.

17 Claims, 1 Drawing Sheet

(51) Int. Cl.
*H01S 3/11* (2006.01)
*H01S 3/10* (2006.01)
*H01S 3/08* (2006.01)
*H01S 3/081* (2006.01)
*H01S 3/092* (2006.01)
*H01S 3/106* (2006.01)
*H01S 3/115* (2006.01)
*A61N 5/06* (2006.01)
*A61B 18/20* (2006.01)
*A61N 5/067* (2006.01)
*A61B 18/00* (2006.01)

(52) U.S. Cl.
CPC .......... *H01S 3/08059* (2013.01); *H01S 3/092* (2013.01); *H01S 3/106* (2013.01); *H01S 3/1103* (2013.01); *H01S 3/115* (2013.01); *H01S 3/1611* (2013.01); *H01S 3/1643* (2013.01); *H01S 3/2308* (2013.01); *H01S 3/2333* (2013.01); *A61B 18/203* (2013.01); *A61B 2018/00452* (2013.01); *A61N 2005/067* (2013.01); *H01S 3/0816* (2013.01); *H01S 3/08063* (2013.01); *H01S 3/10038* (2013.01); *H01S 3/2383* (2013.01); *H01S 2301/206* (2013.01)

(58) Field of Classification Search
CPC ... H01S 5/0615; H01S 3/08063; A61N 5/067; A61N 5/06
USPC .......................................................... 372/12
See application file for complete search history.

(56) References Cited

U.S. PATENT DOCUMENTS

2008/0170597 A1* 7/2008 van der Veer ...... H01S 3/10092
372/29.011
2015/0010036 A1* 1/2015 Salin ...................... H01S 3/082
372/98

* cited by examiner

LASER SYSTEM

CROSS REFERENCE TO RELATED APPLICATION

This application claims priority of European patent application no. 17 001 127.4, filed Jul. 3, 2017, the entire content of which is incorporated herein by reference.

BACKGROUND OF THE INVENTION

In the last few years lasers emitting pulses in sub-nanosecond range entered the dermatology market. Thermal relaxation time of a skin particle is proportional to its size. The sub-ns pulse disrupts a small particle whose thermal relaxation time is in the sub-nanosecond region easier than a pulse with duration of several ns. However, its maximum energy being on the order of several hundreds of mJ is smaller than in the nanosecond region, where it easily enters the J range. Larger particles can be therefore better disrupted with a nanosecond pulse. The optimal laser device intended for skin particles removal should be thus capable to operate with both pulse durations.

A nanosecond pulse with energy in the Joule range can be extracted directly from a laser oscillator for example by a standard Q-switching technique. The origin of the laser oscillation is spontaneously emitted photons within the gain medium. During the energy build up phase the laser oscillation (prelase) is prevented by the Q-switch element. After the Q-switch element is switched to the open state the laser oscillation between the back and forth resonator mirror is allowed and the laser device emits a Q-switched laser pulse. It is outcoupled through a partially transmissive mirror.

Sub-nanosecond pulses can be realized by different techniques. A first option is to use a short laser cavity, usually comprised of two diffusion bonded crystals, where one crystal serves as a gain medium and the other as a passive Q-switch. The faces of the rod are dielectrically coated with reflective layers serving as resonator mirrors. Due to the small volume of the active medium the pulse energy extractable from a microchip cavity is small, usually <1 mJ.

Another approach is to implement a pulse suppression technique. One option is to direct the laser pulse into a cell containing gas with non-linear susceptibility tensor hi. If the pulse is squeezed enough it is scattered in the backward direction. During the stimulated Brillouin scattering the pulse width is suppressed. Pulse width suppression can be achieved also by a fast Pockels cell (EO modulator) inserted between two crossed polarizers.

Regardless of the used technique for the sub-nanosecond pulse generation usually an amplification of its energy is required. Amplification toward several hundred mJ can be achieved in a power amplifier. Arrangement of a master oscillator providing the initial low power pulse characteristics and the power amplifier is abbreviated with MOPA (Master Oscillator Power Amplifier). In a high gain system a sufficient amplification may be achieved by single or double pass of the pulse through the amplifying medium. However, if the gain of the amplifying medium or the seed energy is small, multiple passes are needed. Multiple passes can be achieved in regenerative amplifiers or in special MOPA arrangements.

A double pass amplifier, also called double pass MOPA, usually includes a coupling polarizer, a gain medium, a lambda/4 waveplate and a back reflection mirror. The polarizer reflects the pulse into the amplifier. It passes the amplifying medium followed by the lambda/4 waveplate, and after reflection on the back mirror it passes once again the lambda/4 waveplate and the amplifying medium. A double pass of the lambda/4 waveplate rotates the initial polarization of the pulse by 90 degrees and the polarizer outcouples the amplified pulse.

SUMMARY OF THE INVENTION

It is an object to provide a laser system being capable of delivering two different types of pulsed laser beams with substantially different pulse durations.

This object can, for example, be achieved via the laser system including: a first laser source having a laser resonator for generating a first pulsed laser beam; the laser resonator having a back mirror, an outcoupling mirror and an active lasing medium disposed between the back mirror and the outcoupling mirror; a second laser source for generating a second pulsed laser beam; a first optical block including a coupling polarizer and a first polarization rotator; the first optical block being movable back and forth between an active position and a passive position; the first optical block, in the active position, being disposed between the outcoupling mirror and the active lasing medium such that the coupling polarizer couples the second pulsed laser beam into the laser resonator of the first laser source while the first polarization rotator is positioned between the outcoupling mirror and the coupling polarizer; the first optical block, in the passive position, being disposed such that the first optical block is not interfering with the laser resonator; and, a second polarization rotator configured to be disposed between the first optical block and the back mirror when the first optical block is in the active position.

An embodiment of a laser system includes a first laser source with a laser resonator for generating a first pulsed laser beam, the laser resonator having a back mirror, an outcoupling mirror and an active lasing medium in between. The laser system further includes a second laser source for generating a second pulsed laser beam and a first optical block. The first optical block includes a coupling polarizer and a first polarization rotator, and is movable back and forth between an active position and a passive position. In its active position the first optical block is located between the outcoupling mirror and the active lasing medium such that the coupling polarizer couples the second pulsed laser beam into the laser resonator of the first laser source while the first polarization rotator is positioned between the outcoupling mirror and the coupling polarizer. Furthermore, in the active position of the first optical block a second polarization rotator is located between the first optical block and the back mirror.

Although embodiments are suitable for arbitrary pulse durations of both laser beams generated by the first and second laser sources, preferably the first laser source may be adapted to generate laser pulses with a pulse duration in the nanosecond range, while the second laser source may preferably be adapted to generate laser pulses with a pulse duration in the sub-nanosecond range, in particular in the picosecond range.

Similarly, the first laser source may be adapted to generate laser pulses in the so called long pulse range of 0.05 to 200 msec, while the second laser source may be adapted to generate laser pulses with a pulse duration in the short pulse range of less than 10 microseconds, in spite of the pump pulse duration being longer than 10 microseconds.

Additionally, embodiments are suitable for different wavelengths of both laser beams, providing that both of the laser wavelengths are amplified by the active lasing medium. For example, in case an Nd:YAG laser crystal is being used as the active lasing medium, the applicable wavelengths for each of the two laser beams are 1064 nm, 1320 nm and 1440 nm.

Keeping in mind, that other pulse durations and wavelengths may be used within the scope of the disclosure, for the sake of simplicity the terms "nanosecond" and "sub-nanosecond" are exemplarily used in the following to distinguish between the two different regimes and configurations which the present disclosure seeks to combine.

In its passive position the first optical block has no effect on the laser resonator. The laser resonator of the first laser source includes statically positioned components and is operated as usual and known from prior art to generate a first pulsed laser beam in particular with a pulse duration in the nanosecond range. However, when different pulse durations, in particular shorter pulse durations in the sub-nanosecond range are required, the first optical block is moved into its active position, while the components of the laser resonator remain still in their previous, unchanged position. By inserting the first optical block into the resonator, at least some of the original and existing resonator components including the outcoupling mirror and the active lasing medium are now used with, however, a different function. In this different function the components are used as part of a now configured double pass MOPA for generating amplified pulses in particular with a pulse duration in the sub-nanosecond range.

The seed pulse of the second laser source, preferably a quality switched (Q-switched) pulse is in particular generated in a microchip master oscillator. Its output is linearly polarized and directed toward the polarizer on the first optical block, which couples it into the laser resonator, which now serves as a power amplifier. A first pulse amplification is achieved in passing the active lasing medium of the nanosecond arrangement. Passing the lambda/4 waveplate, reflection and then passing the lambda/4 waveplate a second time, turns the linear polarization of the laser pulse by 90 degrees. After passing the amplifying medium the second time the coupling polarizer transmits the again amplified pulse toward the first polarization rotator of the first optical block. It transforms the linear polarization to a circular polarization. Part of the double pass amplified pulse energy is transmitted through the outcoupling mirror of the original nanosecond laser resonator, while the other part is reflected back towards the amplifier. In the then following second pass the first polarization rotator of the first optical block transforms the circular polarization into a linear polarization. The polarization is now rotated for 90 degrees according to the transmissive direction of the polarizer and is thus prevented to reenter the power amplifier.

Insertion of an optical block including a coupling polarizer and a polarization rotator in a laser cavity which contains an additional polarization rotator on the other side of the amplifying medium is unique. At first glance, the embodiments may follow an unusual approach, since the energy of the amplified pulse in the MOPA arrangement is decreased when passing the polarization rotator and the partially transmissive output mirror on the output side of the resonator. However, despite the losses, the embodiments proves to be very good in terms of optical decoupling of the nanosecond and sub-nanosecond arrangement. The optical settings of the two arrangements are completely independent although the amplifying medium is shared. Thereby, the first optical block has several essential roles.

At first, it serves as a coupler of the pulse into the power amplifier in the MOPA arrangement. In addition, it filters spontaneously emitted photons in the pumping phase of the power amplifier. If not filtered, these emitted photons would be the origin of prelase between the back and forth resonator mirror of the nanosecond arrangement. With the aid of the block the threshold for prelase operation is pushed higher, allowing for unusually high amplification factors. In particular, the outcoupling mirror has a super-Gaussian reflectivity profile. Preferably, the outcoupling mirror may have a central reflectivity in the range from 0.5 to 0.2, preferably in the range from 0.07 to 0.18, and in particular in the range from 0.10 to 0.15, while the active lasing medium is adapted to provide amplification factors for the second pulsed laser beam of >10 and preferably >100. Within the ranges, the output mirror is optimized for the regular resonator mode in the nanosecond range, which however is not optimal for the MOPA mode in the sub-nanosecond range. Despite this fact and the limitation to just two amplification passes, but due to the filtering effect, such high amplification factors of >10 and even >100 can be achieved.

To achieve the equivalent amplified energy without the optical block the outcoupling mirror of the nanosecond arrangement would need to be removed from the optical path in order to push the threshold for the laser operation higher. Obviously the stability of the nanosecond arrangement would be affected.

According to the disclosure, the optical settings of the nanosecond and the sub-nanosecond arrangements do not have mutual influence although both variants share the same amplifying medium. The first optical block switches the device to MOPA operational mode without need to remove any of the optical components of the nanosecond arrangement. This assures stable operation of the nanosecond arrangement without implementation of additional stabilizing mechanisms in the holder of the outcoupling mirror. Mirrors and amplifying medium remain aligned and adjusted without the need for any movement and readjustment. The beam paths of the nanosecond and the sub-nanosecond pulse behind the nanosecond outcoupling mirror are equivalent, so that delivery means like hand pieces and so forth can be used for both configurations without adjustment.

Furthermore, the first optical block prevents the reflected pulse to enter the power amplifier the second time and therefore prevents possible optical breakdown on the optical path. Otherwise the pulse amplified in the next two passes would be directed back toward the master oscillator—the microchip cavity.

The polarization rotators as used within the disclosure can be of any suitable type, provided that the polarization plane of a laser beam after a double pass is rotated by 90°. For achieving the effect the first polarization rotator and/or the second polarization rotator is preferably a λ/4-waveplate or a Pockels cell.

The second polarization rotator as used in the MOPA or sub-nanosecond mode can be a polarization rotator already being present in the resonator of the nanosecond mode, which might be a polarization rotator of a free running resonator or a passive Pockels cell. In case that such a polarization rotator is not available from the resonator of the nanosecond mode for use in the sub-nanosecond MOPA mode, the laser system preferably may include a second optical block, wherein the second optical block includes the second polarization rotator. In analogy to the first optical block, also the second optical block is movable back and forth between an active position and a passive position, and in its active position, the second optical block is located between the first optical block and the back mirror. In its passive position the second optical block has no effect on the laser resonator and allows for an undisturbed nanosecond resonator mode. The optional electro-optical Q-switch allows for the generation of high power nanosecond pulses. In its active position, the desired 90° polarization rotation is achieved, thereby enabling operation in the sub-nanosecond MOPA mode.

In analogy to the second polarization rotator the back mirror as used in the MOPA or sub-nanosecond mode can be the same back mirror as already present in the resonator of the nanosecond mode. In case that such a back mirror is not available from the resonator of the nanosecond mode for use in the sub-nanosecond MOPA mode, as would be the case in an electro-optical Q-switch setup, the second optical block may preferably include a second back mirror in addition to its second polarization rotator. In such case the second optical block in its active position is located between the active lasing medium and the back mirror, preferably between the active lasing medium and the Q-switch, wherein the second polarization rotator is located between the second back mirror and the active lasing medium. That way reflection and double passing of the second polarization rotator by the laser beam is achieved in the sub-nanosecond MOPA mode without disturbing setup and operation in the nanosecond resonator mode.

For the case of the second laser source being adapted to generate laser pulses with a pulse duration in the sub-nanosecond range, and the first optical block being located in its active position, the laser resonator is adapted to be pumped at pump pulse durations of >1 microsecond and in particular of >10 microseconds. Together with an appropriate pulse timing of the active amplifying lasing medium, an individual sub-nanosecond pulse is allowed for a back and forth double pass during one single amplifying lasing medium pulse at optimized high gain level. Typical relaxation oscillations in a laser are on the order to 100 kHz. This implies that a typical rise time from spontaneous emission to high intensity lasing is on the order of 10 microseconds or shorter. It is this time that is needed for the lasing to saturate the medium and to possibly reduce the gain factor G before the seed pulse arrives. Imagine an amplifying medium of the first (base) laser that is pumped for a duration shorter than 10 microseconds. In such a case, the laser intensity will not reach high levels even when $G > G_{thr}$. The gain will continue to grow above $G_{thr}$ until the end of the pumping pulse when the seed pulse will be emitted. In such a case, the mirror reflectivity R would not represent an obstacle in achieving higher amplifications. Therefore embodiments of the present disclosure may be most suitable for pump pulse durations >1-10 microseconds.

The active lasing medium may be any lasing medium suitable for both generating the first pulsed laser beam and amplifying the second laser beam. Preferably, the active lasing medium may be flashlamp pumped, and in particular may include a Nd:YAG crystal and a flash lamp. This makes laser system in particular suitable for dermatology and other medical or cosmetic applications.

The surplus, reflected sub-nanosecond laser energy may be passed to any desired location. Preferably, on the output side of the coupling polarizer a laser energy dump may be positioned such that it receives the laser energy reflected from the outcoupling mirror and from the coupling polarizer. This way the surplus energy and heat can be disposed of in a controlled manner.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
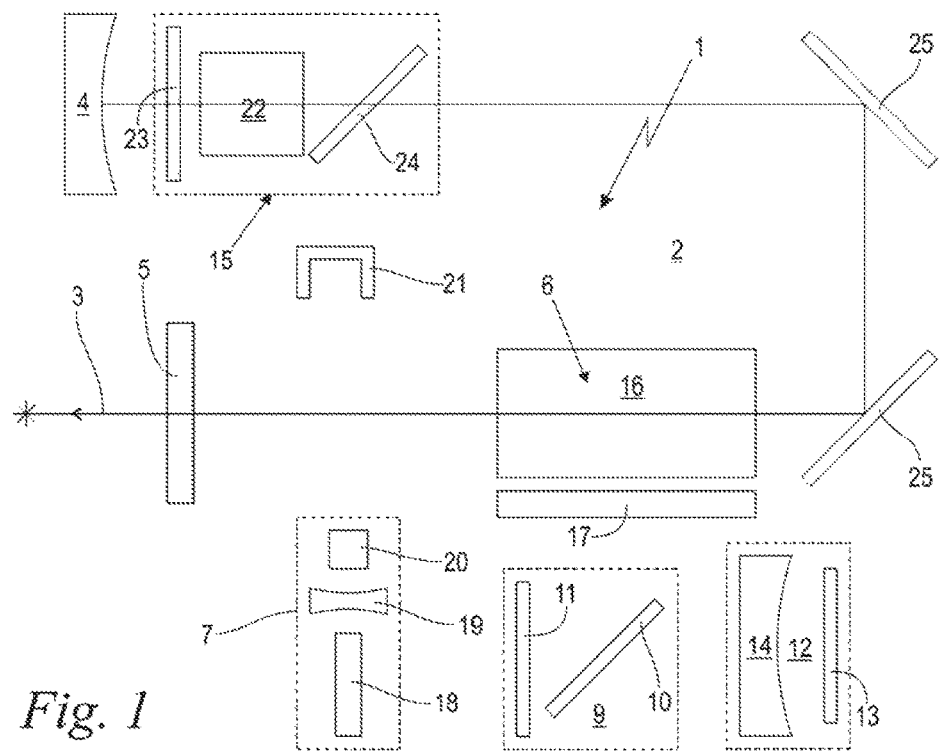
FIG. 1 is a schematic block view of a laser system in a resonator configuration with a laser resonator for generating a first pulsed laser beam with pulse durations in the nanosecond range, and with two additional optical blocks in a passive position; and, FIG. 2 is the laser system of FIG. 1 in a MOPA configuration with the two additional optical blocks moved into their active position for amplifying a second pulsed laser beam.
Figure 2:
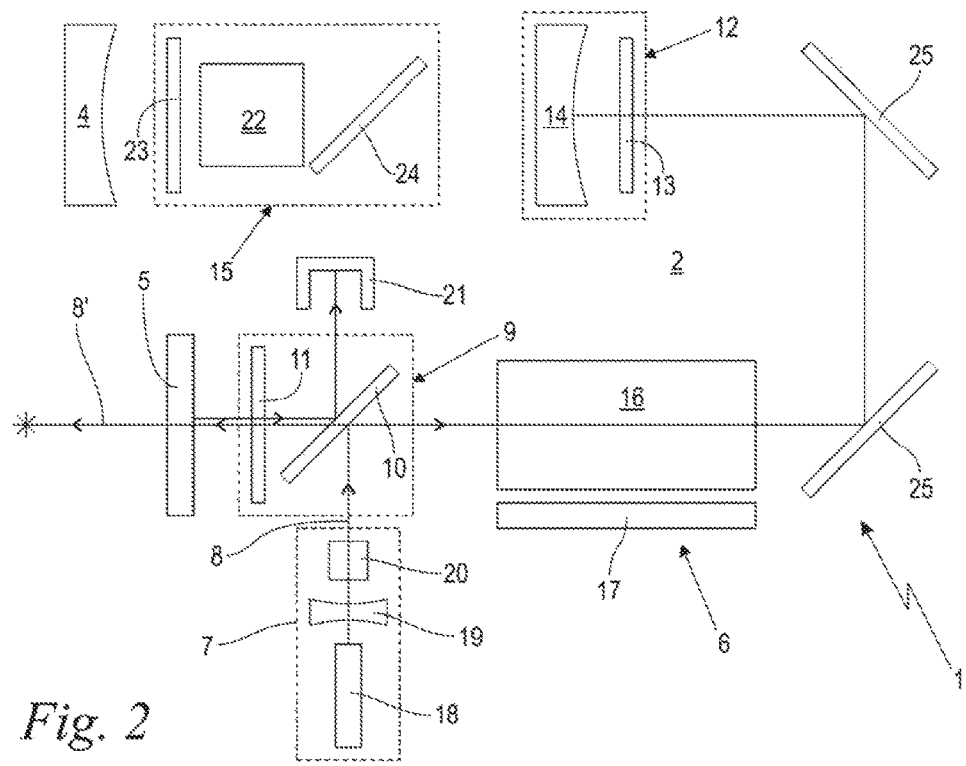

FIG. 1 shows in a schematic block view an embodiment of a laser system including a first laser source 1 with a laser resonator 2 for generating a first pulsed laser beam 3 and a second laser source 7 for generating a second pulsed laser beam 8, 8' (FIG. 2). Furthermore, the laser system includes a first optical block 9, an optional second optical block 12 and an optional laser energy dump 21, the function of which is described in connection with FIG. 2. In FIG. 1 the laser system and in particular the laser resonator 2 are shown in a resonator configuration, in which the second laser source 7 and the laser energy dump 21 are without function, and in which both the first and the second optical block 9, 12 are located in a passive position without interfering with the laser resonator 2.

The laser resonator 2 includes at least a first back mirror 4, an outcoupling mirror 5 and an active lasing medium 6 in between. The back mirror 4 has 100% reflectivity, while the output mirror 5 is partially transmissive, thereby preferably having a super-Gaussian reflectivity profile. Preferable central reflectivities of the back mirror 4 may be in a range from 0.05 to 0.20, even more preferably in the range from 0.07 to 0.18, and in particular in the range from 0.10 to 0.15. In the shown embodiment, the partially transmissive back mirror 4 has a central reflectivity of 0.13. The active lasing medium 6 is flashlamp pumped, and in particular may includes a Nd:YAG crystal 16 and a flash lamp 17. However, other lasing mediums 6 (for example, Er:YAG or alexandrite crystals) and pumping devices (for example, diodes) may be suitable as well.

In the shown resonator configuration of FIG. 1 the first laser source 1 is adapted to generate a first pulsed laser beam 3 with laser pulses each having a pulse duration in the nanosecond range, more precisely in the range from ≥1 nsec to ≥1 μsec. However, other pulse durations, in particular longer pulse durations may be desirable as well. In order to achieve the pulse generation, the laser source 1 includes a quality switch (Q-switch) 15 located between the active lasing medium 6 and the back mirror 4. The Q-switch 15 may be a passive Q-switch. In the present embodiment it is an electro-optical Q-switch 15 including a Pockels cell 22 and a polarizer 24 on the lasing medium side of the Pockels cell 22. Furthermore, the electro-optical Q-switch 15 includes on the back mirror side of the Pockels cell 22 an optional λ/4-waveplate 23 as a polarization rotator. However, within a laser system of the disclosure the Q-switch 15 may be omitted, thereby using the resonator 2 in a free generation mode. For a compact setup, two additional angular mirrors 25 may be provided.

In the shown Q-switched configuration, the active lasing medium 6 is pumped by the flash lamp 17 as well known to a person skilled in the art. This leads to spontaneously emitted photons within the lasing medium 6 being the origin of laser oscillation. During a first energy build up phase the laser oscillation (prelase) is prevented by the Q-switch 15, which is switched to a closed, non-transmissive state by means of the Pockels cell 22. After the Q-switch element is switched to the open, transmissive state the laser oscillation of the emitted photons between the back mirror 4 and the outcoupling mirror 5 is allowed and the laser device emits a Q-switched laser pulse. It is outcoupled through the partially transmissive outcoupling mirror 5 as the above mentioned first pulsed laser beam 3.

FIG. 2 shows the laser system of FIG. 1 in a double pass MOPA (Master Oscillator Power Amplifier) configuration. Therein, the previously described components of the laser resonator 2, in particular the back mirror 4, the outcoupling mirror 5, the active lasing medium 6 including the Nd:YAG crystal 16 and the related flash lamp 17 and the optional Q-switch 15 have not changed their position, thus keeping their previously achieved alignment. However, the first optical block 9 and the optional second optical block 12 have been moved by a suitable, not shown mechanism from their passive position of FIG. 1 to an active position as shown in FIG. 2. Generally, the first and second optical blocks 9, 12 are movable back and forth between their active position of FIG. 2 and their passive position of FIG. 1, thereby switching the laser system and in particular the laser resonator 2 back and forth between the MOPA configuration of FIG. 2 and the resonator configuration of FIG. 1. In the shown embodiment, both the second laser source 7 and the laser energy dump 21 have kept their positions without changes. However, it might be advantageous to move them back and forth together with the first and second optical blocks 9, 12.

The first optical block 9 includes a coupling polarizer 10 and a first polarization rotator 11. In its active position the first optical block 9 is located between the outcoupling mirror 5 and the active lasing medium 6. The second optical block 12 includes a second polarization rotator 13 and an optional second back mirror 14. Together with the first optical block being in its active position, also the second optical block 12 is located in its active position where it is—including its second polarization rotator 13—located between the first optical block 9 and the back mirror 4. In a not shown case, wherein the second optical block 12 does not contain an additional, second back mirror 14, the second optical block 12 including its second polarization rotator 13 may be located in its active position on the front side of the active lasing medium 6, that is between the first optical block 9 and the active lasing medium 6. In the shown embodiment, and in particular with a second back mirror 14 being part of the second optical block 12, the second optical block 12 is in its active position located on the back side of the active lasing medium 6, that is between the active lasing medium 6 and the back mirror 4, more precisely between the active lasing medium 6 and the optional Q-switch 15 such that the second polarization rotator 13 is located between the second back mirror 14 and the active lasing medium 6.

All mentioned polarization rotators are of such type, that a linear polarization of a passing laser beam is turned into a circular polarization, and that a circular polarization of a passing laser beam is turned into a linear polarization, while a double pass rotates the polarization plane of a linear polarization by 90°. For achieving that, the first and second polarization rotators 11, 13 are $\lambda/4$-waveplates. However, other suitable means like Pockels cells may be used as well.

In the shown embodiment the second laser source 7 includes a microchip master oscillator 18 plus an optional expanding lens 19 and an optional Faraday isolator 20 in order to generate a second pulsed laser beam 8, which is linearly polarized at the output of the second laser source 7. However, other suitable types of second laser sources 7 may be chosen as well. The second laser source 7 is adapted to generate a second pulsed laser beam 8 with laser pulses having a pulse duration in the sub-nanosecond range, that is in the picosecond range or even shorter with individual pulse length of <1 nsec.

In practical use, such pulses need amplification, for which the present laser system in the MOPA configuration of FIG. 2 is used. Therefore, in its active position the first optical block 9 is located between the outcoupling mirror 5 and the active lasing medium 6 such that the coupling polarizer 10 couples the second pulsed laser beam 8 into the laser resonator 2 of the first laser source 1 into the direction of the active lasing medium 6, while the first polarization rotator 11 is positioned between the outcoupling mirror 5 and the coupling polarizer 10.

A first pulse amplification of the second laser beam 8 is achieved in passing the active lasing medium 6. Passing the second polarization rotator 13, reflection at the optional second back mirror 14 or the original first back mirror 4, and then passing the second polarization rotator 13 a second time turns the linear polarization of the second laser beam 8 by 90 degrees. Upon passing the active lasing medium 6 a second time the respective pulses of the second laser beam 8 are additionally amplified. In order to achieve the desired amplification in the present MOPA configuration with at least the first optical block 9 being located in its active position, the active lasing medium 6 and in particular the flash lamp 17 of the laser crystal are adapted to be operated at pump pulse durations of >1 microsecond and in particular of >10 microseconds. This allows the individual pulses of the second laser beam 8 for the double amplification pass within one single lasing medium pulse at optimal energy and amplification levels, wherein amplification factors for the second pulsed laser beam 8 of preferably >10 and in particular of >100 are chosen. After the double amplification the coupling polarizer 10 transmits the amplified second laser beam 8 toward the first polarization rotator 11 of the first optical block 9. It transforms the linear polarization to a circular polarization. Part of the double pass amplified pulse energy is transmitted through the outcoupling mirror 5 of the original nanosecond laser resonator 2 as an amplified second laser beam 8', while the other part is reflected back towards the amplifier. In the second pass the first polarization rotator 11 of the first optical block 9 transforms the circular polarization into a linear polarization. The polarization is now rotated by 90 degrees according to the transmissive direction of the coupling polarizer 10 and is thus prevented to reenter the power amplifier. Instead, it is reflected at coupling polarizer 10 into the appropriately positioned laser energy dump 21.

In the shown embodiment the first laser source 1 and the second laser source 7 are adapted to generate first and second pulsed laser beams 3, 8, 8' having the same wavelength. Having chosen the Nd:YAG crystal 16 for the active lasing medium 6, the wavelength is at present 1064 nm. However, a different wavelength can be chosen for both the first and second pulsed laser beams 3, 8, 8' as well. In any case the crystal material of the active lasing medium 6, the reflection properties of first back mirror 4, second back mirror 14 and outcoupling mirror 5, the properties of coupling polarizer 10, and the properties of the first and second polarization rotators 11, 13 are adapted to the required wavelength.

However, within the disclosure it is not necessary that both the first and second pulsed laser beams 3, 8, 8' do have the same wavelength. In particular, several active lasing media 6 do have the capability to work at a number of different wavelengths, one of which can be chosen for the first laser beam 3, and another one of which for the initial second laser beam 8 and the amplified second laser beam 8', if provided with a proper adaptation of second laser source 7, first back mirror 4, second back mirror 14 and outcoupling mirror 5, and the properties of coupling polarizer 10 and the first and second polarization rotators 11, 13. For example, the present Nd:YAG crystal 16 is capable of lasing at 1064 nm, 1320 nm and 1440 nm. This allows to operate the laser system for example at 1064 nm of the first laser beam 3 in the resonator configuration of FIG. 1 and at 1320 nm or 1440 nm for the initial second laser beam 8 and the amplified second laser beam 8' in the MOPA configuration of FIG. 2, provided that the second laser source 7 delivers a seed or initial second laser beam 8 having a wavelength of 1320 nm or 1440 nm.

It should be appreciated that when the first and the second pulse laser beams do not have the same wavelength, the coupling polarizer 10 should be optimized for the first pulsed laser beam 3 and have the reflectivity for the second pulsed laser beams 8, 8' lower than 4%, preferably lower than 0.5%. Additionally, first polarization rotator 11 should be optimized for the wavelength of the first pulsed laser beam 3, and second polarization rotator 13 should be optimized for the wavelength of the second pulsed laser beams 8, 8'.

It is understood that the foregoing description is that of the preferred embodiments of the invention and that various changes and modifications may be made thereto without departing from the spirit and scope of the invention as defined in the appended claims.

What is claimed is:

1. A laser system comprising:
a first laser source having a laser resonator for generating a first pulsed laser beam;
said laser resonator having a back mirror, an outcoupling mirror and an active lasing medium disposed between said back mirror and said outcoupling mirror;
a second laser source for generating a second pulsed laser beam;
a first optical block including a coupling polarizer and a first polarization rotator;
said first optical block being movable back and forth between an active position and a passive position by a means;
said first optical block, in said active position, being disposed between said outcoupling mirror and said active lasing medium such that said coupling polarizer couples said second pulsed laser beam into said laser resonator of said first laser source while said first polarization rotator is positioned between said outcoupling mirror and said coupling polarizer;
said first optical block, in said passive position, being disposed such that said first optical block is not interfering with said laser resonator;
a second polarization rotator configured to be disposed between said first optical block and said back mirror when said first optical block is in said active position;
said laser resonator includes a Q-switch positioned between said back mirror and said active lasing medium;
a second optical block being movable back and forth between a second active position and a second passive position;
said second optical block including said second polarization rotator;

said second optical block, when in said second active position, being disposed between said first optical block and said Q-switch and between said first optical block and said back mirror;
said outcoupling mirror has a central reflectivity ($R_0$) lying in a range from 0.05 to 0.2; and,
said active lasing medium being configured to provide amplification factors for said second pulsed laser beam of >10.

2. The laser system of claim 1, wherein at least one of said first polarization rotator and said second polarization rotator is a $\lambda/4$-waveplate or a Pockels cell.

3. The laser system of claim 1, wherein: said Q-switch is an electro-optical Q-switch.

4. The laser system of claim 1, wherein: said back mirror is a first back mirror; said second optical block includes a second back mirror; and, said second optical block, in said second active position, is disposed between said active lasing medium and said first back mirror.

5. The laser system of claim 1, wherein said outcoupling mirror has a super-Gaussian reflectivity profile.

6. The laser system of claim 1, wherein:
said outcoupling mirror has a central reflectivity ($R_0$) lying in a range of 0.05 to 0.2; and,
said active lasing medium is configured to provide amplification factors for said second pulsed laser beam of >100.

7. The laser system of claim 1, wherein:
said outcoupling mirror has a central reflectivity ($R_0$) lying in a range of 0.07 to 0.18; and,
said active lasing medium is configured to provide amplification factors for said second pulsed laser beam of >10.

8. The laser system of claim 1, wherein:
said outcoupling mirror has a central reflectivity ($R_0$) lying in a range of 0.07 to 0.18; and,
said active lasing medium is configured to provide amplification factors for said second pulsed laser beam of >100.

9. The laser system of claim 1, wherein:
said outcoupling mirror has a central reflectivity ($R_0$) lying in a range of 0.10 to 0.15; and,
said active lasing medium is configured to provide amplification factors for said second pulsed laser beam of >10.

10. The laser system of claim 1, wherein:
said outcoupling mirror has a central reflectivity ($R_0$) lying in a range of 0.10 to 0.15; and,
said active lasing medium is configured to provide amplification factors for said second pulsed laser beam of >100.

11. The laser system of claim 1, wherein:
said first laser source is configured to generate laser pulses with a pulse duration in a nanosecond range; and,
said second laser source is configured to generate laser pulses with a pulse duration in a sub-nanosecond range.

12. The laser system of claim 11, wherein, when said first optical block is disposed in said active position, said active lasing medium is configured to be pumped at pump pulse durations of >1 microsecond.

13. The laser system of claim 11, wherein, when said first optical block is located in its active position, the active lasing medium is adapted to be pumped at pump pulse durations of >10 microseconds.

14. The laser system of claim 1, wherein said active lasing medium is flashlamp pumped.

15. The laser system of claim 1, wherein said active lasing medium is flashlamp pumped and includes a Nd:YAG crystal and a flash lamp.

16. The laser system of claim 1, wherein said second laser source includes a microchip master oscillator.

17. The laser system of claim 1 further comprising:
a laser energy dump;
said coupling polarizer having an output side; and,
said laser energy dump being positioned on said output side of said coupling polarizer such that said laser energy dump receives laser energy reflected from said outcoupling mirror and from said coupling polarizer.

* * * * *